United States Patent [19]

Galanakis

[11] Patent Number: 5,096,696
[45] Date of Patent: Mar. 17, 1992

[54] BINDING OF RADIOLABELED ALBUMIN FRAGMENTS TO FIBRIN CLOTS

[75] Inventor: Dennis K. Galanakis, Stony Brook, N.Y.

[73] Assignee: The Research Foundation of State University of New York, Albany, N.Y.

[21] Appl. No.: 475,359

[22] Filed: Feb. 5, 1990

[51] Int. Cl.$^5$ .................. A61K 49/02; C07K 13/00
[52] U.S. Cl. ........................................ 424/1.1; 530/363
[58] Field of Search ................. 424/1.1; 530/369, 363

[56] References Cited

U.S. PATENT DOCUMENTS

| | | |
|---|---|---|
| 1,371,380 | 3/1921 | Kottmann . |
| 3,674,900 | 7/1972 | Thompson . |
| 3,784,453 | 1/1974 | Dworkin et al. ............. 424/1.1 X |
| 3,803,299 | 4/1974 | Nouel . |
| 3,862,299 | 1/1975 | Bruno et al. . |
| 3,863,004 | 1/1975 | Wolfangel . |
| 3,933,996 | 1/1975 | Charlton et al. . |
| 4,024,233 | 5/1977 | Winchell et al. . |
| 4,094,965 | 6/1978 | Layne et al. . |
| 4,187,285 | 2/1980 | Meeks et al. . |
| 4,226,846 | 10/1980 | Saklad . |
| 4,337,240 | 6/1982 | Saklad . |
| 4,427,646 | 1/1984 | Olexa et al. . |
| 4,636,380 | 1/1987 | Wong ........................ 424/1.1 |
| 4,659,839 | 4/1987 | Nicolotti et al. . |
| 4,663,146 | 5/1987 | Morser et al. . |

OTHER PUBLICATIONS

Weber, M. M., "Albumin Aggregates For Detection of Clots", *Seminars in Nuclear Medicine*, vol. VII, No. 3 (Jul.), pp. 253-261, (1977).

Galanakis et al., "Albumin Modulates Lateral Assembly of Fibrin Polymers: Evidence of Enhanced Fine Fibral Formation and a Unique Synergism With Fibrinogen", *BioChemistry*, vol. 26, No. 8, pp. 2389-2400, (1987).

Kowalsky et al., *Radiopharmaceuticals in Nuclear Medicine Practice*, p. 239, (1987).

*Primary Examiner*—John S. Maples
*Attorney, Agent, or Firm*—Hoffmann & Baron

[57] ABSTRACT

Compositions and methods useful in the diagnosis and treatment of vascular disorders in mammals is disclosed. Intact serum albumin is fragmented by a cleaving agent and thereafter albumin fragments are dissolved in a physiologically acceptable vehicle for therapeutic use or are combined with a radionuclide for use as a diagnostic adjunct in the scanning of mammalian vascular systems.

13 Claims, 1 Drawing Sheet

BINDING OF RADIOLABELED ALBUMIN FRAGMENTS TO FIBRIN CLOTS

BACKGROUND OF THE INVENTION

The present invention relates to diagnosing and possible treatment of vascular disorders, and, in particular, to providing a highly efficient localizing agent which exhibits high affinity for certain vascular disorders.

The clotting of blood as a part of the body's response to an injury or trauma is a part of the natural phenomenon of hemostasis. The clotting of blood, however, may occur in places in the body which produce results which, at times, can be life threatening. Among the more frequent examples of unwanted clotting occurring in the vascular system are those found in the deep veins of the legs or in the lungs. The blockage of blood by a clot in a blood vessel can stop the supply of blood to vital organ systems and other body parts. Equally life-threatening are clots which become dislodged from their original sites and flow through the circulatory system causing blockages at more remote sites. These dislodged clots are called embolisms.

Blood clot formation derives from a series of events, called the coagulation cascade, in which the final steps involve the formation of the enzyme thrombin. Thrombin converts circulating fibrinogen protein into fibrin which in turn forms a mesh-like structure known as the blood clot. The coagulation cascade, (schematically shown in FIG. 1), is highly regulated and involves a series of transformations caused by a succession of zymogen activations, wherein the activated form of one enzyme factor initiates the activation of the next enzyme. The numerous steps of the cascade may be significantly amplified to assure a rapid response to trauma or injury. The cascade is completed when highly soluble fibrinogen is converted by the proteolytic enzyme thrombin into an insoluble fibrin clot.

Under normal hemostatic conditions, a fibrin clot is eventually dissolved by the process of fibrinolysis. As the damaged blood vessel is repaired, the fibrinolytic enzyme plasmin is activated to dissolve the formed fibrin clot.

The detection of blood clots and the subsequent therapeutic dissolution thereof has long been a profoundly important clinical goal, especially since abnormal or pathological clotting is often life threatening and requires medical intervention. Thus, the need for detection and the ability to safely lyse or dissolve pathological clots is of great importance to the medical community. Some affinity of whole or intact albumin, whether in the macroaggregated or microsphere form, for fibrin is known in the art. Common diagnostic uses of the albumin molecule include combining the albumin molecule with a radio isotope for the purposes of obtaining a scintigraphic image of visceral organs.

Albumin is a type of globular protein and is present in mammalian blood and tissues. Albumin is the most abundant protein in human serum and is thought to perform at least two important physiologic functions: osmotic regulation and transportation of fatty acids between adipose tissues.

Most often, when human serum albumin is used for organ imaging, it is denatured by heating so as to produce albumin aggregates of varying particle size and then selectively sieved to obtain the desired particle size. When used diagnostically, albumin is most often combined with a radioisotope, such as technetium-99m or iodine 131, so that scintigraphic images may be obtained. Human albumin microspheres (HAM) and macroaggregated albumin (MAA), are the most common denatured albumin products used diagnostically and such compounds are often referred to as organ imaging agents. Both human albumin microspheres and macroaggregated albumin are denatured by a heating process wherein the albumin protein aggregates in the presence of heat. The denatured albumin is then suspended in a buffered solution before injecting into the vascular system of the patient. U.S. Pat. No. 3,674,900 to Thompson, U.S. Pat. No. 3,803,299 to Nouel, and U.S. Pat. No. 3,862,299 to Bruno, et al., all disclose the use of macroaggregates of serum albumin labeled with a radio nuclide such as technetium-99m for the purposes of studying pulmonary vascular circulation. An article by Webber, "Albumin Aggregates for Detection of Clots", *Seminars in Nuclear Medicine*, Volume VII, No. 3 (July), 253-261, (1977), states that macroaggregates of albumin, (MAA), vary in uptake and that MAA particles from different manufacturers and possibly even from the same manufacturer at various times differ in activity.

U.S. Pat. Nos. 4,337,240 and 4,226,846 to Saklad disclose the use of microaggregates of albumin useful for evaluating the reticuloendothelial system including the liver, lymphatic system and bone marrow. Diagnostic techniques employing the above mentioned albumins and radio nuclides have gained widespread acceptance since their introduction and are an important adjunct to obtaining a definitive diagnosis of vascular pathology. Such products, while useful, are often difficult to prepare and limited in their usefulness. The affinity of albumin for fibrin in mammalian vasculature is weak and difficult to show. This problem often limits the usefulness of this diagnostic modality along with albumin based diagnostic agents since the weak binding will often yield studies of indeterminate result as to the underlying pathology of the suspected vascular block. The lack of intensity with which prior art whole albumin aggregates are able to bind to fibrin in the vascular system therefore limits the usefulness of albumin-based products for diagnostic purposes in cases such as for studies to rule out deep venous thrombosis. Currently, the radionuclide-labeled albumin aggregate-based products are often limited to organ scans such as those of the lung or liver. The high number of indeterminate or inconclusive studies resulting from using albumin aggregate-based products, as known in the prior art, for diagnostic purposes for deep venous thrombosis is attributable to the lack of intense binding of the albumin product to the clot. Thus, the use of such products has failed to meet expectations because of the low level of binding by the albumin-based products at the site of the occlusion, especially in the case of deep venous thrombosis.

The unreliability of albumin based products in diagnosing deep venous thrombi has led to the use of radionuclide-labeled fibrinogen products. U.S. Pat. No. 3,933,996 to Charlton, et al. disclose a composition of albumin and radioactive fibrinogen for detecting thrombi in the deep veins of the leg. Fibrinogen, however, is an inherently unstable material, much more so than other common blood proteins even when precautions have been taken.

To date, radio-labeled products of human serum albumin have also suffered from a lack of stability, an inability to withstand significant changes in pH, and short effective useful lives. Further, difficulties in the heating and controlling of the coagulation of the albumin have lead to difficulty in obtaining economical yields of the particular particle sizes which are generally within the range of 0.1 to 5 microns for microaggregated human serum albumin. On the other hand, macroaggregated human serum albumin, having a particle size of greater than 5 microns but less than 100 microns, may exhibit difficulties in dissolving after introduction into mammalian vasculature due to their particle size.

Kowalsky, et al. in *Radio Pharmaceuticals in Nuclear Medicine Practice*, at page 239, describes the difficulties encountered in the production of albumin microspheres. A small volume of aqueous albumin solution is mixed in a large volume of vegetable oil to produce an emulsion of minute spheres disbursed within the oil. Sphere size is dependent upon mixing speed and the ratio of albumin to the oil. Spheres are then dried and sieved to obtain appropriate particle size. Spheres are then treated with a stannous chloride solution and a radionuclide such as technetium-99m pertechnetate before injection into the vascular system of the subject for study. Other problems include irregularities in particle size, particle number, particle hardness and chemical composition. Further, biodegradation of macroaggregated albumin or human albumin microspheres particles and their radio labels must be regulated so as to provide an ample time for imaging on the one hand, yet once imaging is completed, a somewhat rapid degradation and elimination from the body on the other.

Unlike coagulated, denatured albumin products, albumin which has been cleaved into fragments has not been used in vivo for the purposes of diagnosing vascular system pathology in mammals. The uses for these fragments of albumin have been limited to the study of the albumin molecule structure and in U.S. Pat. No. 1,371,380 to Kottmann, which discloses the preparation of compounds which contain combinations of metals with albumins. Example 13 of the '380 Patent to Kottmann describes the preparation of a compound from iron chloride and placenta albumin which has been treated with trypsin. The compound was then used in vitro as a purported pregnancy test.

The aforementioned approaches and techniques for employing albumin based diagnostic agents all fall short of providing a diagnostic agent which possesses the ability to exhibit a higher percentage of binding of the albumin to the fibrin based pathology in the vascular system of mammals. Further, the prior art fails to provide a reliable albumin based product which is useful in the diagnosis of deep venous thrombosis and is capable of minimizing the number of diagnostic tests for the presence of thrombosis having an indeterminative result.

Accordingly, it is an object of the present invention to provide an effective albumin fragment based diagnostic product detects fibrin found in the vascular system of mammals.

It is also an object of the present invention to provide an agent capable of detecting thrombosis and embolism in patients which is free of the disadvantages of the prior art preparations noted above.

It is a further object of the present invention to provide an albumin fragment based diagnostic product which possesses anticoagulant, anti-fibrinolytic and low clot retraction properties.

A still further object of the present invention is to provide a diagnostic agent which demonstrates a tighter binding to fibrin than is available in the prior art.

Yet another object of the present invention is to provide an efficient high-affinity agent for binding to fibrin along with the advantages concomitant with such high affinity agent such as advancement in treatment of vascular disorders.

Other objects and advantages will become apparent to those skilled in the art from a consideration of the ensuing description which proceeds with reference to the following illustrative claims.

SUMMARY OF THE INVENTION

The present invention includes a method and composition useful in the diagnosis and treatment of vascular disorders. The present invention is directed to a composition suitable for tagging with a radionuclide such as technetium-99m and then introduced into the vascular system of a mammal where a composition of the present invention displays an affinity for fibrin and formed blot clots. When tagged with a radionuclide, therefore, the albumin fragments are useful in the detection of vascular disorders such as thrombosis and embolism.

The invention is further directed to a process for preparing the diagnostic agent. In this process, intact albumin is cleaved into fragments by contacting the intact albumin with a cleaving agent such as cyanogen bromide in solution, or by proteases such as plasmin, elastase, pepsin, papain or trypsin. The cleaving agents are chosen on the basis of being able to selectively cleave the albumin molecule at predetermined positions. Cyanogen bromide, for example, selectively cleaves intact human serum albumin at the position where methionine amino acids are present thereon. The solution containing the now fragmentated albumin is thereafter washed to remove the cleaving agent and then subjected to lyophilization for storage purposes. Sterilization of the fragments may be carried out either prior to lyophilization or prior to diagnostic use according to one's preference. The albumin fragments are later prepared for introduction into the vascular system of mammals by reconstituting the fragments with a buffered, physiologically acceptable solution and later addition of a radionuclide, such as technetium-99m, by methods known in the prior art.

As a result of the present invention, it has been determined that diagnostic evaluations which depend upon for their success definitive scintigraphic confirmation of vascular pathology, such as the presence of thrombosis, are more readily obtainable by introducing into the vascular system of the subject mammal a diagnostic product containing albumin fragments with a radionuclide bound thereto. The product made in accordance with the present invention also exhibits superior fibrin binding capabilities in vivo when compared to that of the prior art. As a result of the present invention, the clinician performing the diagnostic procedure using a diagnostic agent made in accordance with the present invention containing the albumin fragments will obtain more certain results due to the higher percentage binding of the albumin fragments over those made in accordance with the prior art.

Improved therapeutic properties are also provided as a result of the present invention's anticoagulant and antithrombotic properties.

For a better understanding of the present invention, reference is made to the following description and the accompanying drawings, as well as the claims.

DESCRIPTION OF THE PREFERRED EMBODIMENTS

Figure 1:
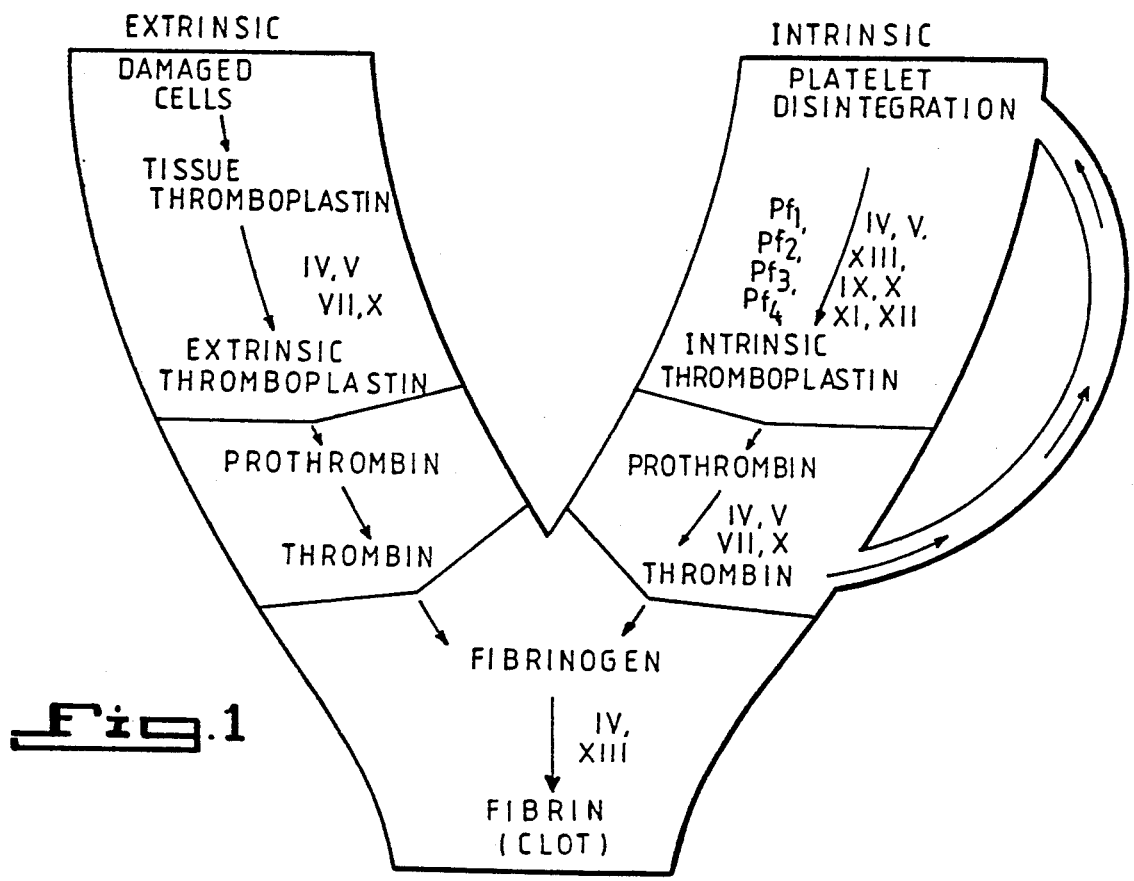
FIG. 1 is a schematic representation of the coagulation cascade showing schematically both the Extrinsic and Intrinsic pathways and their convergence to a common pathway resulting in clot formation, in which thrombin joins with circulating fibrinogen to form fibrin.

The composition of the present invention is characterized by its capacity to provide superior scintigraphic images for the purposes of diagnosing mammalian vascular disorders involving pathologic clotting of fibrin resulting from thromboses and/or emboli. The composition of the present invention is further characterized by containing albumin fragments cleaved from intact, whole albumin obtained from the sera of mammals or other vertebrates.

In a preferred embodiment, the intact, whole albumin is cleaved by contacting the albumin with a solution of a cleaving agent such as cyanogen bromide. The resulting fragments have a molecular weight of from about 3,000 to about 50,000. The fragments are characterized with respect to molecular weight by polyacrylamide gel electrophoresis in sodium dodecyl sulfate buffer against standards of known weight.

The fragments are thereafter cleansed of the cleaving agent, sterilized, and can be lyophilized if needed for extended storage periods.

If the diagnostic properties of the present invention are sought, the fragments are combined with a suitable radionuclide and the resultant radioactive diagnostic product containing albumin fragments is thereafter introduced into the vascular system whereupon vascular occlusions are detectable by gamma radiation detection devices known in the art.

If the therapeutic properties of the albumin fragment based product are sought, the fragments are prepared in a manner similar to the process for the diagnostic use and introduced into the vasculature of the mammal with or without bio-effecting agents attached thereto in quantity sufficient and at a suitable dosage rate to effect the desired treatment. For example, it has been found that albumin fragments prepared in accordance with the present invention can be dissolved in a physiologically acceptable vehicle such as a normal saline based diluent. The solution containing the dissolved albumin fragments may then be introduced into the vascular system of the subject mammal, and has been found to have therapeutic effects. For example, in vitro, a solution containing the fragments has been found to be an effective anticoagulant. Alternatively, the albumin fragments display anti-fibrinolytic properties in vitro by interfering with and/or delaying the dissolution of the fibrin mesh by inhibiting local fibrinolytic enzymes such as plasmin. Such properties could be utilized by placing albumin fragments on localized surgery sites such as tooth extraction sites to reduce or stop bleeding at the site.

Similarly, the albumin fragment based product of the present invention may be used as a carrier of other anticoagulants or clot dissolving agents. The fragments may be prepared to accept these agents in a manner similar to the binding of radionuclides as set forth above in the diagnostic preparation manner. Further, the activity of the therapeutic agents such as anticoagulants are enhanced when combined with the albumin based products of the present invention. Suitable anticoagulants which may be combined with the albumin fragments prepared in accordance with the present invention include for example, warfarin, heparin, antithrombin III or other genetically engineered antithrombins.

By combining known vascularly active compounds such as the therapeutic agents described hereinabove, it can be concluded that the activity of the vascularly active agents is enhanced when combined with the highly efficient fibrin binding capability of products prepared with the present invention. Such combinations, therefore, make possible lower dosage of the therapeutic agents currently used for vascular disorders while at the same time allowing for a significant reduction in the risks associated with their use.

EXAMPLES

The following examples serve to provide further appreciation of the invention but are not met in any way to restrict the effective scope of the claims.

EXAMPLE 1

Whole, intact, human serum albumin, which is available from commercial suppliers as a 5% or 25% solution, was removed from its commercial container by a syringe and placed in a test tube. Thereafter, the albumin was dialyzed for a sufficient time to remove all salts and undesired materials. The albumin was then placed in a 70% formic acid solution, (available from Fisher Chemical). Separately, a 20% cyanogen bromide (available from Merck & Co.) in 70% formic acid solution was prepared. The solution containing the cyanogen bromide should be such that the cleaving agent is present in an amount equal to about a 100-fold molar excess to the methionine present in the albumin protein. The two solutions were thereafter combined and mixed for a sufficient time to effect cleavage of the albumin selectively at the methionine sites. It has been found, for example, that mixing the combined solutions for approximately 2 hours will satisfactorily effect the desired cleavage. It is to be understood that the above procedures are to be carried out in opaque or light-resistant containers, which are known in the art, to protect the reaction from possible undesirable photosensitive changes.

Upon completion of the mixing, the reagent containing the albumin along with the reagent containing the cleaving agent, such as cyanogen bromide, an aliquot of distilled water was added to quench the reaction. The resultant solution was thereafter concentrated by heat evaporation and washed of any remaining excess cleaving agent. The aforementioned concentration step may be successfully carried out by placing the solution in a Rotavapor Model R110 apparatus (manufactured by Büchi) for a period of from about 5 to about 12 hours. The concentrated solution was thereafter dialyzed against a sufficient quantity of distilled water, after which the albumin fragments were lyophilized by standard procedures known in the art and rendered suitable for storage over extended periods in a freezer.

In another embodiment, the albumin fragments were sterilized prior to being placed in the freezer. Sterilization was carried out by known procedures which may include, for example, exposing the albumin fragment solution to high temperatures for an extended period of time, exposure to UV radiation, passing the resultant solution through a microfilter or a combination of these procedures.

In order to prepare for use, the fragments were removed from the freezer and left at ambient temperature for a sufficient time, for example, about 1 hour. The fragments were then reconstituted in a buffered, physiologically acceptable solution. Suitable buffers include phosphate based systems or trisaminomethane. The buffers are needed to adjust the pH of the resultant solution to permit dissolving or solubilizing the fragments, for example, pH ranges of from about 8.0 to 8.5. Physiologically acceptable solutions include, for example, sterile water for injection or normal saline based solutions. The ionic strength of the solution containing the product of the present invention is preferably from about 0.1 to about 0.2.

To this solution, a second solution containing the desired radionuclide was added whereby the radionuclide was bound to the albumin fragment. For example, the albumin fragments may be treated with a divalent metal salt such as stannous chloride to bind the divalent metal to the albumin fragments and provide a means for attaching radioactive material to the fragments. It is also contemplated that radioactive isotopes will be bound to the fragments without a divalent metal. For example, iodine-123 may be directly bound to tyrosine residues found on the albumin fragments.

Radionuclides useful in the diagnosis of mammalian vascular pathology include, for example, technetium-99m, iodine 125, iodine 131, and indium 111, each of which is known for its propensity to be an efficient emitter of gamma radiation within the range needed for the scintigraphic imaging methods known in the art.

Once the solution containing the radionuclide was added to the solution containing the albumin fragments, the resultant product included the albumin fragments "tagged" with a radionuclide. Exceptionally improved scintigraphic imaging of the desired area was possible since the albumin fragments prepared in accordance with the above procedure circulated within the vascular system and became bound to the fibrin at a significantly higher efficiency than previously thought possible with prior art procedures. The radioactive "tag" bound to the highly efficient albumin fragments emits gamma radiation so that the diagnostic imaging devices known in the art are capable of detecting and localizing the area of occlusion.

Since one of the primary purposes of the products of the present invention is its use as a diagnostic agent which is introduced into the vascular system of mammals, the above steps of preparation were carried out under aseptic and nonpyrogenic conditions using sterile containers so that the resultant diagnostic agent could be safely injected into humans as well as other mammals without fear of contaminating the subject.

In accordance with the present invention, the diagnostic agent so prepared is capable of producing superior diagnostic results which are directly attributable to the highly efficient, increased binding of albumin fragments so prepared to fibrin accumulations within the vascular system.

It has also been discovered that the products made in accordance with the present invention can be made to be soluble in the solution which is introduced into the vascular system of the subject. This is a significant departure from the prior art whole albumin-based diagnostic products which were insoluble due to the denaturing process and therefore had to be suspended in a solution. The ability of the product of the present invention to be dissolved in a solution allows for a product, whether diagnostic or therapeutic, to have increased stability once prepared.

EXAMPLE II

The albumin fragments are prepared in a manner similar to that of Example I except that no radionuclide is added to the albumin fragments. The fragments are dissolved in a physiologically acceptable solution which contained a sufficient amount of a trisaminomethane buffer. The dissolved albumin fragments are thereafter combined with fresh whole blood, platelet rich plasma or heparinized plasma, and infused. Alternatively, the fragments may be directly infused into the vascular system of a subject mammal with known vascular occlusion.

Citrated human plasma, heparinized plasma and citrated whole blood samples were each prepared to contain a predetermined amount of the albumin fragments. The clotting times as determined by the visual clotting method, of each of the above samples was thereafter compared to a control sample without albumin fragments. The citrated human plasma and whole blood each contained 5mg/ml of the albumin fragments, while three concentrations of the albumin fragments 2.9, 5.8 and 9.5mg/ml respectively, were tested in heparinized plasma containing 4U/ml of heparin in a 50% buffered solution of Tris HCl physiologic ionic strength, containing 10 millimole, of calcium chloride and reptilase according to standard clotting procedure. The results of the above clotting time comparisons are set forth in Table I.

TABLE I

| Albumin Fragment Concentration | Citrated Human Plasma | | Citrated Whole Blood | | Heparinized Plasma | | | |
|---|---|---|---|---|---|---|---|---|
| | 5 mg/ml | Control (0) | 5 mg/ml | Control (0) | 2.9 mg/ml | 5.8 mg/ml | 9.5 mg/ml | Control (0) |
| Average Clotting Time (seconds) | 28.8 | 12.5 | 28.0 | 10.4 | 27.7 | 36.4 | 53.4 | 19.3 |
| | n = 5 | n = 5 | n = 3 | n = 6 | n = 3 | n = 4 | n = 2 | n = 7 |

Referring now to Table I, it can be seen that the albumin fragments have significant influence on the clotting times of citrated human plasma, citrated whole blood and heparinized plasma. In both plasma and whole blood, 5mg/ml of albumin fragments provided a more than doubling of the clotting time (Plasma, 130% longer; whole blood, 169% longer).

Moreover, with heparinized plasma, the various concentrations show a direct correlation between the concentration of the albumin fragments and length of delay in clotting. As a result of the present invention, the therapeutic benefits of anticoagulation may now be realized either the albumin fragments alone or with combinations of the albumin fragments and reduced amounts of other known anticoagulants.

EXAMPLE III

In this Example, the anti-thrombolytic properties are illustrated. The albumin fragments are prepared in a manner similar to that of Example II and combined with the anti-thrombolytic agent tranexamic acid. The anti-thrombolytic qualities of the albumin fragments were then compared against a control using the triplicate of plasma clots method. The test solution contained a 53% plasma concentration, buffered with Tris HCl physiologic ionic strength, and two millimoles of calcium chloride. The thrombin concentration of the test solution was 3U/ml while the plasmin concentration was 2U/ml. In the absence of albumin fragments, the plasma clots dissolved within 48 hours. However, when 3mg/ml of albumin fragments were added to the test solution, no lysis activity on the clots was observable until after 86 hours. After 5 days, 25% of the original plasma clots were still observable. The test was then stopped at that point and the test solution was discarded. This profound delay in thrombolysis has readily apparent therapeutic advantages, especially in hemorrhagic disorders. The amount of anti-thrombinolytic therapy can be significantly reduced when therapeutic protocols include albumin fragments prepared in accordance with the present invention. Indeed, doses of anti-thrombinolytic agents heretofore thought to be sub-therapeutic, now when combined with albumin fragments, provide significant delay in thrombolysis.

EXAMPLE IV

In this Example, the binding of albumin fragments prepared in accordance with the present invention to fibrin is demonstrated. The albumin fragments were labeled with Iodine-125 and a 155 μg/ml concentration was used to determine the binding of the fragments to fibrin gels, obtainable from fresh plasma or purified fibrinogen, each containing 0.58 mg of fibrin. The fibrin gels were formed in 600 microliter buffers maintaining the solution at a pH of 6.4. Increasing amounts of the above described labelled fragments were added to the fibrin gels, beginning with 1 microliter and proceeding up to 15 microliters. After 10 hours of incubation, the radioactivity of the clots was measured to indicate the amount of albumin fragment binding to the clot.

Figure 2:
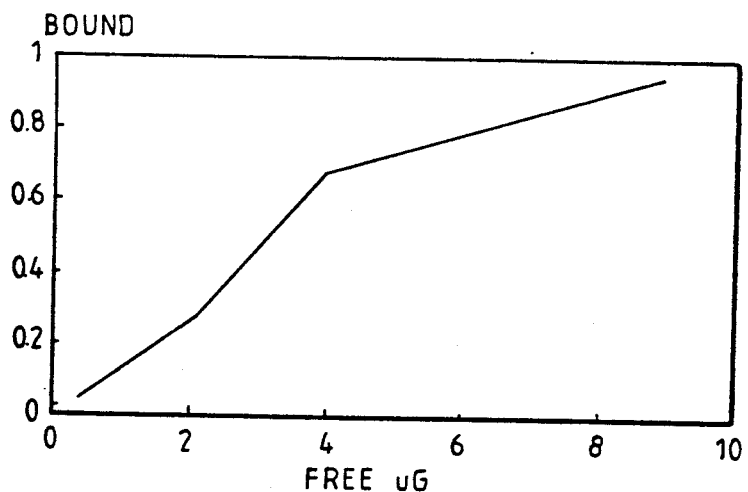
FIG. 2 is a graph showing the binding of albumin fragments to fibrin prepared in accordance with the present invention.

Referring to FIG. 2, it can be seen that albumin fragments, unlike intack albumin which demonstrates no appreciable binding under the same circumstances, not only demonstrates a capacity to bind to fibrin but also that the capacity to bind is concentration dependent. It is believed that superior binding capabilities of the albumin fragments prepared in accordance with the present invention contributes at least in part to the improved diagnostic and therapeutic properties described in the above Examples.

As can be seen from the above Examples, the present invention provides a significant improvement in both the diagnostic and therapeutic capabilities of albumin based products. Diagnostically, the albumin fragments prepared in accordance with the present invention, once introduced into the vascular system, bind to a significantly higher degree to fibrin contained within vascular clots than previously thought possible.

When combined with a radioactive tag, the albumin fragments prepared in accordance with the present invention allow the clinician to obtain significantly more reliable diagnostic images when compared to diagnostic products prepared from whole albumin as was done with the prior art.

Therapeutically, the albumin fragments prepared in accordance with the present invention provide anticoagulant activity useful either as a singular agent or when combined with other known anticoagulant agents. In addition, antifibrinolytic agents can be used in lower doses to treat hemorrphagic disorders because of the effect of albumin fragments of fibrin.

The foregoing description is offered by way of illustration and in fulfillment of the applicant's duty to disclose the best mode for the practice of the invention. Accordingly, the above procedures may be modified within the skill of the art and all such modifications are contemplated herein and made a part hereof.

What is claimed is:

1. A diagnostic agent suitable for detecting the presence of thrombosis or embolism in the vascular system of mammals using scintigraphic imaging, said agent comprising an effective amount of albumin fragments cleaved from intact albumin by a cleaving agent, and a radioactive material bound to said fragments.

2. The diagnostic agent of claim 1, wherein said cleaving agent is selected from the group consisting of cyanogen bromide and proteolytic enzymes.

3. The diagnostic agent of claim 2, wherein said proteolytic enzymes are selected from the group consisting of plasmin, elastase, pepsin, trypsin, papain and mixtures thereof.

4. The diagnostic agent of claim 1, wherein said radioactive material is selected from the group consisting of technitium-99m, iodine 125, iodine 131 and indium 111.

5. The diagnostic agent of claim 4, wherein said radioactive material is bound to said albumin fragment by a divalent metal.

6. A method of localizing fibrin in mammals comprising the steps of:
   (a) cleaving intact albumin with a cleaving agent, into fragments;
   (b) binding a radioactive material to said fragments;
   (c) adjusting the pH of said fragments to a range suitable for introduction into mammalian vascular systems;
   (d) introducing an effective amount of said fragments obtained from step (c) into the vascular system of mammals whereby said fragments contact and bind to fibrin; and
   (e) scanning said mammals whereby said radioactive material bound to said albumin fragments indicates areas of fibrin accumulation.

7. The method of claim 6, wherein said radioactive material is selected from the group consisting of technetium-99m, iodine 125, iodine 131 and indium 111.

8. The method of claim 6, wherein the pH of said albumin fragments is adjusted by addition of a phosphate buffer.

9. The method of claim 6, wherein the pH of said albumin fragments is adjusted by addition of trisaminomethane buffer.

10. The method of claim 6, wherein said cleaving agent is selected from the group consisting of cyanogen bromide and proteolytic enzymes.

11. The method of claim 7, wherein said proteolytic enzymes are selected from the group consisting of plasmin, elastase, trypsin, pepsin, papain and mixtures thereof.

12. The method of claim 6, wherein said radioactive material is bound to said albumin fragments by a divalent metal ion.

13. The method of claim 10, wherein said divalent metal is stannous.

* * * * *